| United States Patent [19] | [11] Patent Number: 5,008,097 |
| --- | --- |
| Yamashita | [45] Date of Patent: * Apr. 16, 1991 |

[54] AQUEOUS SOLUTION CONTAINING A NEW FERRIC FERROUS SALT $Fe_2Cl_5$ AND METHOD OF PRODUCING SAME

[75] Inventor: Shoji Yamashita, Nagoya, Japan

[73] Assignee: I.B.E. Co., Ltd., Aichi, Japan

[*] Notice: The portion of the term of this patent subsequent to Jan. 10, 2006 has been disclaimed.

[21] Appl. No.: 227,626

[22] Filed: Aug. 2, 1988

Related U.S. Application Data

[63] Continuation-in-part of Ser. No. 655,220, Sep. 27, 1984, abandoned.

[30] Foreign Application Priority Data

Mar. 6, 1984 [JP] Japan .................................. 59-43209
Sep. 18, 1984 [JP] Japan ................................ 59-195287

[51] Int. Cl.$^5$ ....................... B32B 15/04; C01G 49/10
[52] U.S. Cl. .................................... 423/493; 427/435; 428/472.2
[58] Field of Search ............... 423/275, 463, 472, 493; 75/0.5 R, 0.5 A, 0.5 AA, 114, 251, 300, 392, 711, 230; 422/8, 13, 14; 427/435; 428/472.2

[56] References Cited

U.S. PATENT DOCUMENTS 4,797,156  1/1989  Yamashita et al. .................... 75/114

OTHER PUBLICATIONS

Bailar et al., *Chemistry*, Academic Press, 1978, pp. 23-24, 375-376, 381-383.
Mellor, *A Comprehensive Treatise on Inorganic and Theoretical Chemistry*, Longmans, Green and Co., 1935, p. 106.

*Primary Examiner*—Jeffrey E. Russel
*Attorney, Agent, or Firm*—Cooper & Dunham

[57] ABSTRACT

An aqueous solution containing a new ferric ferrous salt $Fe_2Cl_5$ and a method of producing the same are provided. Said aqueous solution contianing said $Fe_2Cl_5$ may include both the aqueous solution of said $Fe_2Cl_5$ and the aqueous mixture of said $Fe_2Cl_5$ and a salt of alkali metals or a compound containing a metal which belongs to zinc family. A method of producing said $Fe_2Cl_5$ comprises dissolving ferric chloride into aqueous solution of sodium hydroxide and then neutralizing said resulting aqueous solution by hydrochloric acid or dissolving ferrous sulfate into aqueous solution of hydrochloric acid, and a method of producing said aqueous mixture comprises adding said $Fe_2Cl_5$ into an aqueous solution of strong acid and then adding a salt of alkali metals or a compound containing a metal which belongs to zinc family. Said aqueous solution containing said $Fe_2Cl_5$ may be very useful in a wide variety of fields, such as water cleaning, keeping freshness of vegetation, antisepsis, antifungi, antibacteria, rust preventing, effluent treatment, soil improvement, ionization control, feed enriching, petroleum improvement, antistatic technique, and the like.

11 Claims, No Drawings

AQUEOUS SOLUTION CONTAINING A NEW FERRIC FERROUS SALT $Fe_2Cl_5$ AND METHOD OF PRODUCING SAME

This application is a continuation-in-part application of Ser. No. 655,220 filed Sept. 27, 1984 now abandoned.

BACKGROUND OF THE INVENTION

1. Field of the Invention

The present invention relates to an aqueous solution containing a new ferric ferrous salt $Fe_2Cl_5$ and a method of producing the same. More particularly the present invention relates to an aqueous solution of said $Fe_2Cl_5$ and an aqueous mixture of said $Fe_2Cl_5$ a salt of alkali metals or a compound containing a metal which belongs to zinc family. Furthermore, the invention relates to a method of producing said $Fe_2Cl_5$ comprises dissolving ferric chloride into aqueous solution of sodium hydrochloride and then neutralizing said resulting aqueous solution by hydrochloric acid or dissolving ferrous sulfate into aqueous solution of hydrochloric acid and a method of producing said aqueous mixture comprising adding said $Fe_2Cl_5$ into an aqueous solution of strong acid and then adding a salt of alkali metals or a compound containing a metal which belongs to zinc family.

2. Description of the Prior Art

Hitherto, $2FeCl_2.FeCl_3.xH_2O$ and $FeCl_2.2FeCl_3.xH_2O$ have been known as ferric ferrous chlorides, and said ferric ferrous chlorides have been known to have adsorption ability. Further, it has been elucidated by the invention of the present invention that said ferric ferrous chlorides have bioactivity. Nevertheless, said bioactivity, adsorption ability, and the like of said ferric ferrous chlorides are not remarkable and therefore said ferric ferrous chlorides have never been to put to practical use.

SUMMARY OF THE INVENTION

Accordingly, an object of the present invention is to provide a new ferric ferrous salt which has remarkable bioactivity, adsorption ability, and the like.

Another object of the present invention is to utilize the special character of said new ferric ferrous salt in a wide variety of fields.

Further object of the present invention is to provide a method of producing an aqueous solution containing said new ferric ferrous salt.

Briefly, these objects of the present invention can be attained by an aqueous solution of a new ferric ferrous salt $Fe_2Cl_5$ and an aqueous mixture of said $Fe_2Cl_5$ and a salt of alkali metals or a compound containing a metal which belongs to zinc family and by a method of producing said $Fe_2Cl_5$ comprises dissolving ferric chloride into aqueous solution of sodium hydroxide and then neutralizing said resulting aqueous solution by aqueous hydrochloric acid or dissolving ferrous sulfate into aqueous solution of hydrochloric acid, and a method of producing said aqueous mixture comprising adding said $Fe_2Cl_5$ into an aqueous solution of strong acid and then adding a salt of alkali metals or a compound containing a metal which belongs to zinc family.

DETAILED DESCRIPTION

A new ferric ferrous salt $Fe_2Cl_5$ of the present invention may be prepared by the following method:

1. From ferric chloride

Ferric chloride is dissolved into aqueous solution of sodium hydroxide and then said solution is neutralized by aqueous hydrochloric acid. The resulting neutralized solution is evaporated to obtain crystal. The crystal is collected and dissolved into isopropanol-water mixture. The resulting solution is filtered and then concentrated to obtain crystal.

2. From ferrous sulfate

Ferrous sulfate is dissolved into HCl aqueous solution and then the resulting solution is concentrated to obtain crystal. Said crystal is collected and dissolved into isopropanol-water mixture. The resulting solution is filtered and then concentrated to obtain crystal.

Said crystal obtained by said method 1 and 2 is identified as follows:

1. Preparation of a test solution A

A solution is prepared by dissolving said crystal in the distilled water at 0.1% (weight/volume). 25 ml of said solution is put into a 50 ml measuring flask and 2.5 ml of o-phenanthroline aqueous solution (0.1% (weight/volume)) and 2.5 ml of sodium acetate-acetic acid buffer (pH 4.5) is added to said test solution in said flask, and further the distilled water is added to adjust the total volume of the resulting mixture to 50 ml. Said adjusted mixture is kept at the room temperature for 30 minutes to obtain a test solution A.

2. Preparation of a comparative solution

A ferrous chloride solution as a comparative solution is prepared by the same method as said test solution A.

3. Determination of absorbance of the test solution A

Absorbance of said test solution A is determined and the concentration of ferrous ion is obtained from the absorbance curve of said comparative solution. As the result, it is determined that 0.019% (weight/volume) of ferrous ion is contained in said test solution A.

4. Preparation of a test solution B

When said crystal is dissolved in the distilled water in the preparing process of the test solution A, further 1.0 ml of the aqueous solution of hydroxylamine-HCl (10% (weight/volume)) is added to reduce ferric ion contained in said crystal to ferrous ion.

5. Determination of absorbance of the test solution B

Absorbance of said test solution B is determined the same as the test solution A and the concentration of ferrous ion is obtained the same as the test solution A. As the result, it is determined that 0.038% (weight/volume) of ferrous ion is contained in said test solution B.

6. Calculation of the concentration of the ferric ion in said crystal.

As above determined, the concentration of the ferrous ion in the test solution A is 0.019% (weight/volume) and the concentration of the ferrous ion in the test solution B is 0.038% (weight/volume) and therefore, the concentration of the ferric ion is 0.038−0.019=0.019 (weight/volume). This means that the ferrous ion is equivalent to the ferric ion in said crystal.

7. Confirmation of the unity

5% (weight/volume) aqueous solution of said crystal is analyzed by the paper chromatography employing n-butanol:acetic acid:distilled water mixture (1:1:1 volume) as the solvent and 1% (weight/volume) aqueous solution of potassium ferricyanide as a color developper. As the result, Rf value of said crystal is 0.07 while Rf value of ferrous ion is 0.095 and Rf value of ferric ion is 0.36.

According to said identification, it is identified that said crystal is not a mixture of ferric chloride and ferrous chloride but an united compound $FeCl_2 \cdot FeCl_3$ ($Fe_2Cl_5$) and said $Fe_2Cl_5$ is dissolved in the distilled water to produce the aqueous solution of the present invention. In the present invention, an aqueous mixture of said $Fe_2Cl_5$ and a salt of alkali metals or a compound containing a metal which belongs to zinc family is also provided. Said $Fe_2Cl_5$ may be stabilized by said salt of alkali metals or compound containing a metal which belongs to zinc family in said aqueous mixture. Said aqueous mixture may be prepared by adding said salt of alkali metals or said compound containing a metal which belongs to zinc family to an aqueous solution of said $Fe_2Cl_5$.

Salt of alkali metals in the present invention may be such as KCl, NaCl, LiCl, $K_2SO_4$, $Na_2SO_4$, $Li_2SO_4$, $CH_3COOK$, $CH_3COONa$, $CH_3COOLi$ and the like, and a compound containing a metal which belongs to zinc family in the present invention may be such as $ZnCl_2$, $CdCl_2$, $ZnSO_4$, $CdSO_4$, $(CH_3COO)_2Zn$, $(CH_3COO)_2Cd$, ZnO, CdO, $Zn(OH)_2$, $Cd(OH)_2$ and the like.

Further, a desirable method of producing said aqueous mixture of the present invention is a one-step method wherein said $Fe_2Cl_5$ is produced in the presence of a salt of alkali metal or a compound containing a metal which belongs to zinc family.

One of desirable one-step methods of the present invention is as follows: Ferrous sulfate is dissolved into HCl aqueous solution and further, sodium chloride or a compound containing a metal which belongs to zinc family is dissolved into said solution. The resulting solution is concentrated to obtain crystal. Said crystal is collected and dissolved into methanol and the resulting solution is filtered and then concentrated to obtain purified crystal. The resulting purified crystal is further purified by washing with pyridine, and then recrystallized by ethanol and said further purified crystal is dissolved in the distilled water to obtain the aqueous mixture of the present invention. Said aqueous solution of said $Fe_2Cl_5$ or said aqueous mixture (aqueous solution containing $Fe_2Cl_5$) of the present invention is used singly or as complex with other materials in a wide variety of fields, such as water cleaning, keeping freshness of vegetation, antisepsis, antifungi, antibacteria, rust preventing, effluent treatment, soil improvement, ionization control, feed enriching, petroleum improvement, antistatic technique, and the like. In said aqueous solution containing $Fe_2Cl_5$ of the present invention, other material, such as aluminium, sodium chloride, vegetable fiber, protein is added to the compound comprising ferric ferrous salt and a salt of alkali metals. Said material to be added should be selected according to purposes of use of said aqueous solution containing $Fe_2Cl_5$ of the present invention.

Further, it becomes clear that metals treated by the aqueous solution of the present invention possess amplified and/or altered special character. Said metals to be treated by the aqueous solution of the present invention may be such as Fe, Cu, Al, and the like. For said treatment, powder, flakes, particles, strip, and the like of said metal is soaked into the aqueous solution of the present invention, and then said metal is separated from said solution. In said treatment, existence of carbon, silica compound, such as silicate, silicon oxide, and the like, or material containing silica such as zeolite, sand, and the like increases and/or alters the effect of the treatment.

EXAMPLE 1

Preparation of $Fe_2Cl_5$

One gram of ferrous sulfate ($FeSO_4 \cdot 6H_2O$) was put into 5 ml of 12N HCl aqueous solution and after sufficient agitation insoluble materials in said solution were removed by filtration using filter paper (No. 5C). Said solution was concentrated in vacuum. The resulting residue was collected and dissolved into 10 ml of methanol and said methanol solution was dried in a desiccator. The resulting dried material was washed with a small amount of pyridine and then crystallized in 10 ml of ethylalcohol. 10.4 mg of $Fe_2Cl_5$ was obtained in the form of fine crystal.

EXAMPLE 2

Preparation of the Original Solution A 10.4 mg of $Fe_2Cl_5$ prepared by Example 1 was dissolved into 1 liter of water and further, 10 g of ferric chloride ($FeCl_3 \cdot 6H_2O$) was added into said solution. To obtain the original solution, the resulting solution was diluted by water ($1000\times$).

EXAMPLE 3

Preparation of Aluminium Complex 0.5 ml of concentrated aqueous HCl was added into 500 ml of the original solution A obtained in Example 2 and aluminium powder was added into the resulting solution. After sufficient agitation, said solution with dispersed said aluminium powder was kept for 24 hours and then said treated aluminium powder was separated from the solution. Said separated aluminium powder was further put into the original solution A in which 0.5 g of caustic soda and 0.5 g of glucose were added and after sufficient agitation, said solution with dispersed said aluminium powder was kept for 24 hours. Said treated aluminium powder was separated from the solution and dried to obtain the complex A-1.

EXAMPLE 4

Preparation of Sodium Chloride Complex 5 g of the complex A-1 and 10 g of glucose was added into 10 liter of sea water and said treated sea water was kept for more than 5 days. Said treated sea water was filtered by using filter paper (No. 5C) and 2 liters of said filtered sea water was put into an enameled vessel. 500 g of sodium chloride was added into said treated sea water in the enameled vessel and dissolved completely by heating at 50° C. and further, 1 mg of the complex A-1 was added. The resulting solution was evaporated by heating until the volume of said solution decreased to 200 ml and crystallized sodium chloride complex (the complex A-2) was obtained during said evaporation. The resulting complex A-2 was dried in a vacuum dryer.

EXAMPLE 5

Preparation of Magnesium Chloride Complex

After the complex A-2 was collected in Example 4, the remaining solution was further concentrated on the water bath until the volume of said solution decreased to 20 ml and crystallized materials were removed from said concentrated solution. Magnesium chloride ($MgCl_2.6H_2O$) was added into the remaining solution to make a saturated solution of magnesium chloride. Said saturated solution was used as magnesium chloride complex (the complex A-3).

EXAMPLE 6

Preparation of Vegetable Fiber Complex 100 g of material containing a large amount of vegetable fiber, such as beet pulp, droppings of Herbivora, and the like was suspended in 1 liter of water and then 1 g of the complex A-1 was added. After sufficient agitation, said mixture was kept overnight and then heated at a temperature below 100° C. to dry. The vegetable fiber complex (the complex A-4) was finally obtained in the form of the dried powder.

EXAMPLE 7

Preparation of Soybean-Protein Complex 100 g of soybean-protein was suspended in 1 liter of water and then 1 g of the complex A-1 was added. After sufficient agitation, said mixture was kept overnight and then heated at a temperature below 100° C. to dry. The soybean-protein complex (the complex A-5) was finally obtained in the form of the dried powder.

EXAMPLE 8

Preparation of $Fe_2Cl_5$—NaCl Compound

One gram of ferrous sulfate ($FeSO_4.6H_2O$) was put into 5 ml of 12N HCl aqueous solution and after sufficient agitation insoluble materials in said solution were removed by filtration using filter paper (No. 5C). Sodium chloride (0.1 g) was added into said filtered solution and said solution was concentrated in vacuum. The resulting residue was collected and dissolved into 10 ml of methanol and said methanol solution was dried in a desiccator. The resulting dried material was washed with a small amount of pyridine and then crystallized in 10 ml of ethylalcohol. 10.6 mg of $Fe_2Cl_5$—NaCl compound was obtained in the form of fine crystal.

EXAMPLE 9

Preparation of the Original Solution B 10.6 mg of $Fe_2Cl_5$—NaCl compound prepared by Example 8 was dissolved into 1 liter of water and further, 10 g of ferric chloride ($FeCl_3.6H_2O$) was added into said solution. To obtain the original solution, the resulting solution was diluted by water (1000×).

EXAMPLE 10

Preparation of Aluminium Complex 0.5 ml of concentrated aqueous HCl was added into 500 ml of the original solution B obtained in Example 9 and aluminium powder was added into the resulting solution. After sufficient agitation, said solution with dispersed said aluminium powder was kept for 24 hours and then said treated aluminium powder was separated from the solution. Said separated aluminium powder was further put into the original solution B in which 0.5 g of caustic soda and 0.5 g of glucose were added and after sufficient agitation, said solution with dispersed said aluminium powder was kept for 24 hours. Said treated aluminium powder was separated from the solution and dried to obtain the complex B-1.

EXAMPLE 11

Preparation of Sodium Chloride Complex 5 g of the complex B-1 and 10 g of glucose was added into 10 liters of sea water and said treated sea water was kept for more than 5 days. Said treated sea water was filtered by using filter paper (No. 5C) and 2 liters of said filtered sea water was put into an enameled vessel. 500 g of sodium chloride was added into said treated sea water in the enameled vessel and dissolved completely by heating at 50° C. and further, 1 mg of the complex B-1 was added. The resulting solution was evaporated by heating until the volume of said solution decreased to 200 ml and crystallized sodium chloride complex (the complex B-2) was obtained during said evaporation. The resulting complex A-2 was dried in a vacuum dryer.

EXAMPLE 12

Preparation of Magnesium Chloride Complex

After the complex B-2 was collected in Example 11, the remaining solution was further concentrated on the water bath until the volume of said solution decreased to 20 ml and crystallized materials were removed from said concentrated solution. Magnesium chloride ($MgCl_2.6H_2O$) was added into the remaining solution to make a saturated solution of magnesium chloride. Said saturated solution was used as magnesium chloride complex (the complex B-3).

EXAMPLE 13

Preparation of Vegetable Fiber Complex 100 g of material containing a large amount of vegetable fiber, such as beet pulp, droppings of Herbivora, and the like was suspended in 1 liter of water and then 1 g of the complex B-1 was added. After sufficient agitation, said mixture was kept overnight and then heated at a temperature below 100° C. to dry. The vegetable fiber complex (the complex B-4) was finally obtained in the form of the dried powder.

EXAMPLE 14

Preparation of Soybean-Protein Complex 100 g of soybean-protein was suspended in 1 liter of water and then 1 g of the complex B-1 was added. After sufficient agitation, said mixture was kept overnight and then heated at a temperature below 100° C. to dry. The soybean-protein complex (the complex B-5) was finally obtained in the form of the dried powder.

EXAMPLE 15

Use of the Complex A-1 and B-1

100 g of the complex A-1 and B-1 were respectively put in a bag A and a bag B of nylon cloth and said bas A and bag B containing respectively the complex A-1 and B-1 were respectively suspended in water in a concrete tank A and a concrete tank B of which capacity were respectively 20 tons. In spite that said water to be treated had high concentration of iron and silicate, no duck weeds propagated in said water during the treatment in both tanks A and B and said treated water stayed clear and fresh in tank B and said treated water become a little muddy in tank A from May to August. Further, no rust and scales were found on the surface of the metal pipe in both tanks A and B.

EXAMPLE 16

Use of the Complex A-2 and B-2

The cut ends by the root of greens such as Chinese cabbage, lettuce, spinach, and the like were soaked in 1 ppm aqueous solution of the complex A-2 and B-2 respectively for 30 min and after soaking, said soaked parts of greens were respectively covered with vinyl chloride films. Said treated greens stayed fresh for one week in the case of the complex B-2 and 5 days in the case of the complex A-2 at room temperature while untreated greens withered within 3 days.

EXAMPLE 17

Use of the Complex A-3 and B-3, No. 1

The original solution A was prepared by diluting the complex A-3 first with distilled water at $10^8 \times$ and then with sea water at $100 \times$. The original solution B was also prepared the same as the original solution A. Said original solutions A and B were respectively added into emulsion A and B of cutting oil at 1/1000 in volume and said treated emulsion A and B were respectively kept at 30° C. No microorganisms propagated in both emulsions A and B and the emulsion B did not denature for more than 35 days and the emulsion A did not denature for more than 25 days while many microorganisms propagated in the flake A untreated controlled emulsion and said untreated emulsion completely coagulated after 5 days.

EXAMPLE 18

Use of the Complex A-3 and B-3, No. 2

The original solution A and B of Example 17 were respectively diluted with distilled water at $1000 \times$ and the sawdust, aluminium flake, and sea sand were respectively soaked in said diluted solution A for 24 hours. Said treated sawdust A, aluminium flake A, and sea sand A were respectively separated from said solution A and dried. Sawdust B, aluminium flake B, and sea sand B were also obtained by treatment with the diluted solution B. 50 g of mixture of said sawdust A and said aluminium (50:1 weight ratio) were put into a glass column (diameter 3.5 cm) and effluent (BOD 9100 mg/liter) from a sugar refining factory was put through said glass column at the rate of 50 ml/minute. Further, said effluent was put through a glass column (diameter 3.5 cm) at the rate of 50 ml/minute containing 100 g of mixture of said sea sand A and said aluminum flake A (100:1 weight ratio) and the BOD of the treated effluent decreased to 26 mg/liter. On the other hand, in the case of same treatment using said sawdust B, said aluminium flake B and said sea sand B, the BOD of the treated effluent decreased to 14 mg/liter.

EXAMPLE 19

Use of the Complex A-3 and B-3, No. 3

8 liters of sea water was put into a plastic vessel and 1 g of said sawdust A of Example 18 was added to said sea water. A graphite plate ($19.5 \times 10$ cm) as an anode and a copper plate ($19.5 \times 10$ cm) as a cathode were respectively inserted into said treated sea water. The distance between anode and cathode was 35 cm and 0.2 volt direct current was charged to said electrodes while air was blown into said sea water while charging the direct current. Immediately a large amount of white clots and brown clots were formed around and/or on the cathode and a metal film was formed on the surface of the sea water. After charging the direct current for 48 hours, no chlorine ion was detected in the resulting sea water A. The same result is obtained in the case of the sea water B treated by said sawdust B of Example 18.

EXAMPLE 20

Use of the Complex A-3 and B-3, No. 4

Rice plants were cultivated by using only the sea water A and B of Example 19 respectively and no hindrance to the growth of rice plants was observed in both cases of the sea water A and B.

EXAMPLE 21

Use of the Complex A-4 and B-4

300 g of the complex A-4 was mixed into soil of 10 a of the nursery A and 300 g of the complex B-4 was mixed into soil of 10 a of the nursery B the same as the nursery A, and seedlings of rice plant were respectively cultivated in said nursery A and B by using the ordinally method. Said seedlings A from the nursery A and said seedlings B from the nursery B were respectively replanted to rice field A and rice field B and excellent growth of said both seedlings A and B was recognized without the stem forking. 742 kg of rice about seedlings A and 793 kg of rice about seedlings B were harvested per 10 a of said rice field A and B while only 480 to 510 kg of rice was harvested per 10 a of the untreated controlled rice field.

EXAMPLE 22

Use of the Complex A-5 and B-5

0.1% of the complex A-5 was mixed with the feed A and 0.1% of the complex B-5 was mixed with the feed B and said feed A and B were respectively administered to cows with no appetite. In both cases, the appetite of said cows respectively increased very much and said cows recovered from the mastitis-like condition, and two to three days after administering of the feed A and B, the cow's milk production increased by about 10%.

EXAMPLE 23

Treatment of Filter (1) Preparation of treating solutions

I. 5 g of ferric chloride ($FeCl_3.6H_2O$) was added into 50 ml of the original solution A and further, the solution wherein 23 g of caustic soda was dissolved in 50 ml of water was added into said solution. The distilled water was added into the resulting solution to increase the solution to the total amount of 200 ml. Thus, the first solution A was prepared. The first solution B was prepared by the same process using the original solution B.

II. 5 g of ferric chloride ($FeCl_3.6H_2O$) was added into 50 ml of the original solution A and further, 50 ml of the concentrated HCl aqueous solution was added into said solution to increase the solution to the total amount of 100 ml. Thus, the second solution A was prepared. The second solution B was prepared by the same process using the original solution B.

III. The complex A-3 was diluted by the distilled water at $10^8$ X and further, the resulting diluted solution was diluted by sea water at 100 X. Thus the third solution A was prepared. The third solution B was prepared by the same process using the original solution B.

(2) Treatment of filter

Three vessels containing respectively 10 liters of distilled water were prepared, and 10 ml of said first solution A, said second solution A and said third solution A were respectively added into each vessel to prepare the first treating solution A, the second treating solution A, and the third treating solution A. A filter was soaked in the first treating solution A for 3 hours; second treating solution A for 3 hours; and the third treating solution A, more than 10 hours. Thus the treated filter A was obtained. The treated filter B was obtained by the same process using said first solution B, said second solution B and said third solution B.

EXAMPLE 24 use of the treated filter A and B

Subterranean water containing a large amount of iron component was filtered by using the treated filter A of Example 23 and radishes were water-cultured by using said treated water. As the result, the rate of growth of said radishes increased, and decay by microorganisms was completely prevented and high grade radishes were obtained. The same result was obtained in the case that the treated filter B is used. The radishes cultured by untreated water were somewhat decayed and their growth was slow.

EXAMPLE 25 treatment of plastic film (1) Preparation of the treating solution A and B

The complex A-3 was diluted by the distilled water to $10^8$ X and further, said solution was diluted by sea water to 100 X. 5 ml of the resulting solution, 5 g of citric acid, and 10 g of the complex A-5 were added to 4995 ml of distilled water and after sufficient agitation, an iron piece (5×7 cm) wherein 0.5 ml of acetic acid salt of α-tocopherol was applied respectively on both surfaces of said iron piece was immersed in the resulting solution and kept overnight at room temperature. Then, said iron piece was removed from the solution and said solution was vacuum-filtered by the filter paper (No. 5C). The resulting filtered solution was used as the treating solution A. The treating solution B is obtained the same process using the complex B-3 and the complex B-5.

(2) Treatment of plastic film

The treating solution A was applied on the surface of the film of polyvinyl chloride and the resulting film was dried to obtain the film A and the film B was obtained by applying the treating solution B on the surface of the film of polyvinylchloride. The freshness test of fruit and vegetable by using said treated film A and B was carried out as follows: Bananas were wrapped with said treated film A and B respectively and kept at 30° C. Said wrapped bananas stayed fresh for three days in both cases of the film A and B while bananas wrapped with the untreated controlled film turned black in the most parts of the peelings and some eatable parts of bananas decayed in one day. Spinach and leeks were respectively wrapped with said treated film A and B and no color change of spinach and leeks were recognized and they stayed fresh after three days in both cases of the film A and B, while spinach and leeks wrapped with the untreated controlled film remarkably withered.

EXAMPLE 26

Preparation of Ferric Ferrous Chloride -$ZnCl_2$ Compound 1 g of ferrous sulfate ($FeSO_4.6H_2O$) was put into 5 ml of 12N HCl aqueous solution and after sufficient agitation, insoluble materials in said solution was removed by filtration using filter paper (No. 5C). 0.1 g of zinc chloride was added into said filtered solution and said solution was concentrated in vacuum. The resulting residue was collected and dissolved into 10 ml of methanol and said methanol solution was dried in a desiccator. The resulting dried material was washed with a small amount of pyridine, and then crystallized in 10 ml of ethylalcohol. 15.2 mg of ferric ferrous chloride-$ZnCl_2$ compound was obtained in the form of fine crystal.

EXAMPLE 27

Preparation of the Original Solution C

One gram of ferric ferrous chloride-$ZnCl_2$ of Example 26 was dissolved into 50 ml of the distilled water, and further, 4 g of ferric chloride ($FeCl_3.6H_2O$) was added into said solution. To obtain the original solution C, the concentrated HCl aqueous solution was added to the resulting solution to increase the solution to the total amount of 100 ml.

EXAMPLE 28

Recovering of Insulation Oil

Copper piece (5×10 cm) was immersed in the diluted original solution C ($10^6$ X), and said copper piece was taken out from said solution after immersing for 24 hours. The treated copper plate was inserted into denatured insulation oil and kept for 10 days at room temperature. After said treatment, said copper piece was taken out from the insulation oil and the electric breakdown endurance of said treated insulation oil was determined for four samples. The result is shown in Table 1. The numbers in Table 1 show the electric breakdown endurance of the insulation oil (K.V.).

TABLE 1

| | Sample No. | | | | |
|---|---|---|---|---|---|
| | 1 | 2 | 3 | 4 | average |
| Treated oil | 50< | 50< | 50< | 50< | 50 |
| Untreated oil (control) | 30 | 28 | 32 | 27 | 29.3 |

Preferring to Table 1, it may be clear that said insulation oil was recovered to the same quality as fresh oil.

EXAMPLE 29

Antistatic Agent of Textile

A polyester cloth (100 $cm^2$) was soaked in the diluted original solution C ($10^6$ X) and kept for 24 hours. After treating for 24 hours, said polyester cloth was taken out from said solution and dried. The frictional charge voltage and its half-valved period about said treated polyester cloth were determined. The results are shown in Table 2.

TABLE 2

| Sample | Frictional charge voltage (V) | Half-valved period |
|---|---|---|
| Treated cloth | 24 | 4.0 |
| Untreated cloth | 7800 | more than 180 |

TABLE 2-continued

| Sample | Frictional charge voltage (V) | Half-valved period |
|---|---|---|
| (control) | | |

EXAMPLE 30

Improvement of Crude Petroleum

An iron piece (5×10 cm) was immersed in the diluted original solution C ($10^6$ X), and said iron piece was taken out from said solution after immersing for 24 hours. Said treated iron piece was inserted into crude petroleum and kept for 2 hours at room temperature. After said treatment, said iron piece was taken out from the crude petroleum and the combustion test of said treated crude petroleum was carried out. As the result, less oil soot was produced and better igniting effectiveness was obtained comparing with untreated crude petroleum. The results of the analysis of the treated crude petroleum are shown in Table 3.

TABLE 3

| | |
|---|---|
| Water content (by KF method) | 172 ppm |
| Ash content | 0.01% |
| Carbon residue | 0.23% |
| Sulfur content | 0.03% |
| Nitrogen content | 0.08% |
| Specific gravity (15/4° C.) | 0.7805 |
| API degree (60° F.) | 49.72 |
| Kinematic viscosity (30° C.) | 1.193 Cst |
| Flash point (TAG) | −39.0° C. |
| Flow temperature | −42.5° C. |
| Heating valve | 11050 cal/g |

EXAMPLE 31

Improvement of Lubricating Oil

An iron ring was immersed in the diluted original solution C ($10^6$ X) and said iron ring was taken out from said solution after immersing for 24 hours. The following friction test was carried out: The surfaces of a pair of T.P. soft steel plate were respectively contacted with the upper and lower parts of a shaft rotating at 373 rpm while loading the weight of 6.5 kg with supplying said treated lubricating oil to the contacting surfaces. After contacting with said loading for 8 hours, the valve of [Reduced thickness]×[length of contacting part] of said T.P. soft steel plate which contacted with the upper part of said shaft was $14 \times 10^{-2} [mm]^2$ and while said valve of the untreated controlled lubrication oil was $30 \times 10^{-2} [mm]^2$.

EXAMPLE 32

Effluent Treatment 3 kg of iron scraps were immersed in 5 liters of the diluted original solution C ($10^6$ X) and said iron scraps were taken out from said solution after immersing for 48 hours. Said iron scraps were put on the coarse sand layer (thickness 10 cm, sectional area 2.3 m²) in a column. Said three columns were combined in series and effluent containing raw sewage, effluent from kitchens and the like was continuously put through said three columns at the rate of 1 ton per day. After treating for 3 days, treated effluent became clear and the treatment of said effluent was proven to be satisfactory. The quality of the treated effluent after treating for 5 days is shown in Table 4.

TABLE 4

| Quality | Before treatment | After treatment |
|---|---|---|
| BOD (mg/liter) | 8480 | 2.0 |
| COD (mg/liter) | 1360 | 0.5 |
| SS (mg/liter) | 56 | 0 |
| Extract with n-haexan (mg/liter) | 488 | 0.3 |
| The number of E. coli/cm³ | $4.3 \times 10^6$ | 0 |
| Phosphoric ion (mg/liter) | 5.2 | 0.1 |

EXAMPLE 33

Antisepsis and Antifungi 0.1 g of iron powder and 1 ml of soy sauce were added into 25 ml of the diluted original solution C ($10^6$ X) and after sufficient agitation, said mixture was kept overnight. Then, said mixture was filtered through the filter paper (No. 5C) and 1 ml of said filtrate was added into 1 liter of soy sauce diluted 2× with water and said mixture was continuously agitated by the magnetic stirrer at room temperature. After agitating for 3 weeks, no propagation of fungi or bacteria was recognized in the treated soy sauce and the flavor of the treated soy sauce also did not change, while remarkable propagation of fungi and bacteria and putrefaction were recognized in the untreated controlled soy sauce.

EXAMPLE 34

Rust Preventing 0.1 g of iron powder and 0.1 g of carbon powder were added into the diluted original solution C ($10^6$ X), and after 24 hours, said mixture was filtered through filter paper (No. 5C). An iron piece (5×10 cm) gathering rust was immersed in 150 ml of said filtrate for 24 hours. For the evaluation for rust preventing, said treated iron piece was immersed in sea water for 30 days. The surface of said treated iron piece became dark and no increase of rust was recognized, while a remarkable increase of rust was recognized on the surface of the untreated controlled iron piece.

EXAMPLE 35

Deodorizing

Four impingers were connected in series and 350 ml of the diluted original solution C ($10^6$ X) was respectively put in the first, second, third impingers and 150 ml of the diluted original solution C was put in the fourth impinger. The distance between foaming plate of the impinger and surface of the solution was respectively controlled about 8 to 9 cm. Four types of gas to be treated were respectively put through said four impingers and smell concentration for each treated gas was determined. Smell concentration is defined as magnification of diluting when no smell of the treated gas is detected while diluted with air. The results are shown in Table 5.

TABLE 5

| Treating time (min) | gas A | gas B | gas C | gas D |
|---|---|---|---|---|
| Untreated | 5000 | 5000 | 50000 | 20000 |
| 3 | 100> | 173 | 2000 | 100> |
| 30 | 100> | 214 | 2500 | 100> |

TABLE 5-continued

| Treating time (min) | gas A | gas B | gas C | gas D |
|---|---|---|---|---|
| 60 | 100> | 424 | 2500 | 100> |

Gas A: exhaust gas from the mixing process of raw rubber.
Gas B: exhaust gas from the boiling process of materials of beer.
Gas C: exhaust gas from the boiling process of materials of beer.
Gas D: exhaust gas from the fermenting process of yeast.

Referring to Table 5, it may be clear that the compound of the present invention has a remarkable and durable deodorizing effectiveness.

I claim:

1. An aqueous solution of a new ferric ferrous salt $Fe_2Cl_5$.

2. An aqueous solution in accordance with claim 1, wherein said $Fe_2Cl_5$ is produced by a method which comprises dissolving ferric chloride into aqueous solution of sodium hydroxide and then neutralizing said resulting aqueous solution with aqueous hydrochloric acid.

3. An aqueous solution in accordance with claim 1, wherein said $Fe_2Cl_5$ is produced by a method which comprises dissolving ferrous sulfate into an aqueous solution of hydrochloric acid.

4. An aqueous mixture comprising $Fe_2Cl_5$ and either a salt of alkali metals or a compound containing a metal which belongs to zinc family.

5. An aqueous mixture in accordance with claim 4, wherein said salt of alkali metals is sodium chloride, and said compound containing a metal which belongs to zinc family is zinc chloride.

6. A method of preparing the aqueous mixture of claim 4 comprising; dissolving a ferrous salt into an aqueous hydrochloric acid solution, and further, dissolving a salt of alkali metals or a compound containing a metal which belongs to the zinc family.

7. A method in accordance with claim 6, wherein said ferrous salt is ferrous sulfate, said salt of alkali metals is sodium chloride, said compound containing a metal which belongs to zinc family is zinc chloride.

8. A method of preparing the aqueous mixture of claim 4 comprising; dissolving ferrous sulfate into an aqueous solution of hydrochloric acid, further, dissolving sodium chloride or zinc chloride into said solution, concentrating the resulting solution to obtain crystal, collecting and dissolving said crystal into methanol, drying the resulting solution in a desiccator and dissolving the resulting crystal in distilled water.

9. A method in accordance with wherein the resulting crystal recovered from methanol is further washed with pyridine and then recrystallized by ethanol.

10. A metal treated by the aqueous solution of claim 1.

11. A metal treated by the aqueous mixture of claim 4.

* * * * *